United States Patent
Nguyen et al.

(10) Patent No.: US 11,826,217 B2
(45) Date of Patent: Nov. 28, 2023

(54) DENTAL MOUTHPIECE

(71) Applicant: Solmetex, LLC., Northborough, MA (US)

(72) Inventors: Thien Nguyen, Santa Ana, CA (US); Tam Thanh Pham, San Francisco, CA (US); Ethan Nguyen, Santa Ana, CA (US); Lauren Nguyen, Santa Ana, CA (US)

(73) Assignee: Solmetex, LLC., Northborough, MA (US)

( * ) Notice: Subject to any disclaimer, the term of this patent is extended or adjusted under 35 U.S.C. 154(b) by 0 days.

(21) Appl. No.: 16/870,745

(22) Filed: May 8, 2020

(65) Prior Publication Data

US 2020/0352680 A1  Nov. 12, 2020

Related U.S. Application Data

(60) Provisional application No. 62/846,353, filed on May 10, 2019.

(51) Int. Cl.
*A61C 5/90* (2017.01)
*A61B 1/24* (2006.01)
(Continued)

(52) U.S. Cl.
CPC .................. *A61C 5/90* (2017.02); *A61B 1/24* (2013.01); *A61C 7/08* (2013.01)

(58) Field of Classification Search
CPC ........... A61C 5/90; A61C 17/08; A61C 17/06; A61C 17/04; A61C 17/043;
(Continued)

(56) References Cited

U.S. PATENT DOCUMENTS

| 50,461 A | 10/1865 | Dibble |
|---|---|---|
| 1,471,207 A | 10/1923 | Napoleon |

(Continued)

FOREIGN PATENT DOCUMENTS

| CA | 2851861 | 2/2016 |
|---|---|---|
| CA | 3139689 | 11/2020 |

(Continued)

OTHER PUBLICATIONS

He, Qing-xuan, "CN 104490483 A_Translated" (Year: 2015).*

(Continued)

*Primary Examiner* — Heidi M Eide
*Assistant Examiner* — Holly T. To
(74) *Attorney, Agent, or Firm* — POLSINELLI LLP (57) ABSTRACT

A dental mouthpiece is provided that may be attached to a high-suction dental adapter for the purpose of assisting the dental staff during dental procedures through chair-side, hands-free suction, and isolation. Such a mouthpiece may comprise a main body portion, a cheek retractor portion, and a suction connector portion. In an embodiment, the main body portion, cheek retractor portion, and suction connector portion may be molded in one piece, preferably by injection molding. The main body portion has an anterior wall inside the curve and a posterior wall outside the curve, and an at least one connector connecting the anterior wall and the posterior wall. The main body portion has an anterior intervening wall and the posterior intervening wall in between the anterior and posterior walls. The anterior intervening wall and the posterior intervening walls have alternating crests and troughs.

23 Claims, 10 Drawing Sheets

(51) Int. Cl.
*A61C 17/08* (2006.01)
*A61C 7/08* (2006.01)

(58) Field of Classification Search
CPC ....... A61C 17/0208; A61C 17/10; A61B 1/24;
A61B 1/0094; A61B 2017/22079
USPC ................ 433/92, 91, 93, 136, 138, 140, 20
See application file for complete search history.

(56) References Cited

U.S. PATENT DOCUMENTS

| | | | |
|---|---|---|---|
| 1,731,322 A | 10/1929 | Riddle | |
| 2,019,612 A | 11/1935 | Langhans et al. | |
| 2,937,445 A | 5/1960 | Erickson | |
| 3,090,122 A | 5/1963 | Erickson | |
| 3,453,735 A | 7/1969 | Burt et al. | |
| 3,516,160 A | 6/1970 | Leffler et al. | |
| 3,758,950 A | 9/1973 | Krouzian | |
| 3,768,477 A | 10/1973 | Anders et al. | |
| 3,802,081 A | 4/1974 | Rogers | |
| 3,857,181 A | 12/1974 | Rappaport | |
| 3,877,691 A * | 4/1975 | Foster | A61M 16/009 5/600 |
| 3,924,333 A * | 12/1975 | Erickson | A61C 17/08 433/93 |
| 4,017,975 A | 4/1977 | Johnson | |
| 4,024,642 A | 5/1977 | Zorovich | |
| 4,083,115 A | 4/1978 | McKelvey | |
| 4,167,814 A | 9/1979 | Schubert | |
| 4,192,071 A | 3/1980 | Erickson | |
| D267,586 S | 1/1983 | Hatlen | |
| 4,511,329 A | 4/1985 | Diamond | |
| 4,718,662 A | 1/1988 | North | |
| 4,802,851 A | 2/1989 | Rhoades | |
| 4,822,278 A | 4/1989 | Oliva et al. | |
| 4,975,057 A | 12/1990 | Dyfvermark | |
| 5,009,595 A | 4/1991 | Osborn | |
| 5,037,298 A | 8/1991 | Hickham | |
| 5,078,602 A | 1/1992 | Honoshofsky | |
| 5,460,524 A | 10/1995 | Anderson | |
| D364,456 S | 11/1995 | Solnit et al. | |
| 5,516,286 A | 5/1996 | Kushner | |
| 5,588,836 A | 12/1996 | Landis et al. | |
| 5,720,275 A * | 2/1998 | Patil | A61M 16/0488 128/200.24 |
| 5,730,599 A | 3/1998 | Pak | |
| 5,762,496 A | 6/1998 | Albertsson et al. | |
| 5,890,899 A | 4/1999 | Sclafani | |
| 6,022,214 A | 2/2000 | Hirsch et al. | |
| 6,213,772 B1 | 4/2001 | Costello | |
| 6,241,521 B1 | 6/2001 | Garrison | |
| 6,267,591 B1 | 7/2001 | Barstow | |
| 6,338,627 B2 | 1/2002 | Hirsch et al. | |
| 6,575,746 B2 | 6/2003 | Hirsch et al. | |
| 6,652,276 B2 | 11/2003 | Fischer et al. | |
| 6,655,960 B2 | 12/2003 | Fischer | |
| 6,672,305 B2 * | 1/2004 | Parker | A61M 16/0495 128/200.26 |
| 6,716,029 B2 | 4/2004 | Fischer et al. | |
| D495,799 S * | 9/2004 | Hirsch | D24/108 |
| D497,426 S | 10/2004 | Hirsch | |
| 6,908,308 B2 | 6/2005 | Hirsch et al. | |
| 6,974,321 B2 * | 12/2005 | Hirsch | A61C 17/08 433/93 |
| 7,287,981 B2 | 10/2007 | Hirsch | |
| 7,293,990 B2 | 11/2007 | Hirsch et al. | |
| 7,611,354 B2 | 11/2009 | Hirsch et al. | |
| D615,203 S * | 5/2010 | Hirsch | A61C 17/10 D24/152 |
| 7,748,981 B2 | 7/2010 | Hirsch et al. | |
| 8,029,280 B2 | 10/2011 | Black et al. | |
| 8,057,227 B2 | 11/2011 | Hirsch et al. | |
| 8,057,228 B2 | 11/2011 | Hirsch et al. | |
| 8,075,310 B2 | 12/2011 | Hirsch et al. | |
| D663,831 S | 7/2012 | Sidhu et al. | |
| D666,726 S | 9/2012 | Davis et al. | |
| 8,297,973 B2 | 10/2012 | Hirsch et al. | |
| 8,529,256 B2 | 9/2013 | Hirsch et al. | |
| 8,535,056 B2 | 9/2013 | Dragan et al. | |
| D696,779 S | 12/2013 | Hirsch et al. | |
| 8,911,232 B2 | 12/2014 | Nguyen | |
| D734,851 S | 7/2015 | Nguyen | |
| 9,084,656 B2 | 7/2015 | Hirsch | |
| 9,089,389 B2 | 7/2015 | Hirsch et al. | |
| D735,858 S | 8/2015 | Hirsch et al. | |
| D737,964 S | 9/2015 | Jessop et al. | |
| 9,358,086 B2 | 6/2016 | Hirsch | |
| D782,047 S | 3/2017 | Ritter | |
| D782,048 S | 3/2017 | Ritter | |
| D787,069 S | 5/2017 | Ritter | |
| D787,070 S | 5/2017 | Ritter | |
| 9,788,924 B2 | 10/2017 | Nguyen | |
| D809,660 S | 2/2018 | Nguyen | |
| 9,968,341 B2 | 5/2018 | Ritter | |
| 10,390,734 B2 * | 8/2019 | Johnson | A61C 19/04 |
| 10,390,916 B1 * | 8/2019 | Rassibi | A61C 17/092 |
| D868,958 S | 12/2019 | Reyes | |
| D876,627 S | 2/2020 | Nguyen | |
| 10,939,979 B2 | 3/2021 | Lombardi | |
| D962,438 S | 8/2022 | Nguyen | |
| D962,439 S | 8/2022 | Nguyen | |
| 11,576,764 B2 | 2/2023 | Nguyen | |
| 11,589,969 B2 | 2/2023 | Nguyen | |
| 11,589,970 B2 | 2/2023 | Nguyen | |
| 11,744,686 B2 | 9/2023 | Nguyen et al. | |
| 2001/0008752 A1 | 7/2001 | Hirsch et al. | |
| 2003/0134253 A1 | 7/2003 | Hirsch et al. | |
| 2004/0033468 A1 | 2/2004 | Fischer et al. | |
| 2006/0063126 A1 | 3/2006 | Aloise et al. | |
| 2006/0063129 A1 * | 3/2006 | Hirsch | A61C 17/10 433/93 |
| 2006/0084031 A1 | 4/2006 | Hirsch et al. | |
| 2008/0166684 A1 | 7/2008 | Kanas | |
| 2008/0318183 A1 | 12/2008 | Suzman | |
| 2009/0123886 A1 | 5/2009 | Vaska | |
| 2009/0274991 A1 * | 11/2009 | Black | A61C 17/08 433/93 |
| 2011/0207076 A1 | 8/2011 | Hirsch et al. | |
| 2011/0311942 A1 | 12/2011 | Black et al. | |
| 2012/0015317 A1 * | 1/2012 | Milo | A61C 17/08 433/29 |
| 2012/0015320 A1 | 1/2012 | Koo | |
| 2012/0237894 A1 | 9/2012 | Maycher et al. | |
| 2013/0095450 A1 | 4/2013 | Ames | |
| 2013/0252193 A1 | 9/2013 | Bowman et al. | |
| 2014/0004478 A1 | 1/2014 | Hirsch et al. | |
| 2014/0162209 A1 * | 6/2014 | Nguyen | A61C 17/0208 433/93 |
| 2014/0212837 A1 | 7/2014 | Nguyen | |
| 2014/0212838 A1 | 7/2014 | Nguyen | |
| 2014/0212839 A1 | 7/2014 | Nguyen | |
| 2014/0212840 A1 | 7/2014 | Nguyen | |
| 2014/0212841 A1 * | 7/2014 | Nguyen | A61C 17/0208 433/93 |
| 2014/0349249 A1 * | 11/2014 | Reyes | A61C 17/08 433/96 |
| 2015/0305842 A1 | 10/2015 | Hirsch et al. | |
| 2015/0335409 A1 * | 11/2015 | Hirsch | A61C 5/90 433/93 |
| 2017/0156831 A1 * | 6/2017 | Reyes | A61C 17/08 |
| 2017/0156832 A1 * | 6/2017 | Reyes | A61C 17/08 |
| 2017/0156833 A1 * | 6/2017 | Reyes | A61C 5/90 |
| 2018/0153637 A1 * | 6/2018 | Al-Shawi | A61B 90/40 |
| 2020/0155284 A1 * | 5/2020 | Baker | A61C 17/10 |
| 2020/0383560 A1 | 12/2020 | Day | |
| 2022/0378563 A1 * | 12/2022 | Cao | A61C 17/084 |

FOREIGN PATENT DOCUMENTS

| | | | |
|---|---|---|---|
| CN | 102026587 | 4/2011 | |
| CN | 102247140 | 11/2011 | |
| CN | 104490483 A * | 4/2015 | A61C 17/04 |
| CN | 105578986 A | 5/2016 | |

(56) References Cited

FOREIGN PATENT DOCUMENTS

| EP | 2903557 | | | 8/2015 | | |
|---|---|---|---|---|---|---|
| EP | 3184076 | | | 6/2017 | | |
| EP | 3965637 | | | 3/2022 | | |
| FR | 2992161 | A1 | * | 12/2013 | ............... | A61C 5/90 |
| GB | 2 170 106 | | | 7/1986 | | |
| JP | 2022-533276 | | | 7/2022 | | |
| KR | 100654392 | B1 | * | 12/2006 | | |
| TW | 202108088 | | | 3/2021 | | |
| WO | WO 1999/037238 | | | 7/1999 | | |
| WO | WO-0042939 | A1 | * | 7/2000 | ............... | A61C 5/90 |
| WO | WO-0061031 | A1 | * | 10/2000 | ............. | A61C 17/08 |
| WO | WO 2011/014952 | | | 2/2011 | | |
| WO | WO 2015/088577 | | | 6/2015 | | |
| WO | WO-2018126150 | A1 | * | 7/2018 | ............... | A61C 5/82 |
| WO | WO 2020/231864 | | | 11/2020 | | |

OTHER PUBLICATIONS

PCT Application No. PCT/US2014/032892 International Preliminary Report on Patentability dated Jun. 14, 2006.
PCT Application No. PCT/US2020/032228 International Search Report and Written Opinion dated Aug. 12, 2020.
U.S. Appl. No. 14/228,046; Non-Final Office Action dated Oct. 6, 2021.
U.S. Appl. No. 14/228,054; Office Action dated Jun. 25, 2021.
U.S. Appl. No. 14/228,057; Final Office Action dated Nov. 12, 2021.
U.S. Appl. No. 29/782,645; Non-Final Office Action dated Oct. 4, 2021.
U.S. Appl. No. 29/782,638; Non-Final Office Action dated Oct. 4, 2021.
U.S. Appl. No. 29/782,644; Non-Final Office Action dated Oct. 4, 2021.
U.S. Appl. No. 29/782,643; Non-Final Office Action dated Oct. 4, 2021.
Dryshield brochure. Dryshield.com. Publish date: May 2019. Retrieval date: Sep. 15, 2021. Retrieved from internet: https:// dryshield.com/ds/Brochure_May2019.pdf (Year: 2019).
"Dryshield Presentation (Learn all about Dryshield)" posted by Dryshield Isolation System. Youtube. Posting date: Oct. 27, 2014. Retrieval date: Sep. 15, 2021. Retrieved from internet: https://www.youtube.com/watch?v=fcbpz3ixvis (Year: 2014).
"Dryshield (single-use) vs Zryis/Isolite (single-use) mouthpieces" posted by Mark Frias, RDH. Youtube. Posting date: Jan. 18, 2020. Retrieval date: Sep. 15, 2021. Retrieved from internet: https://www.youtube.com/watch?v=uKX9XahO6EY (Year: 2020).
"Dryshield Tutorial—Maximize Your Dryshield Experience" posted by Dryshield Isolation System. Youtube. Posting date: Apr. 15, 2015. Retrieval date: Sep. 15, 2021. Retrieved from internet: https://www.youtube.com/watch?v=L2OSYPS8Rc4 (Year: 2015).
PCT Application No. PCT/US2014/032892 International Search Report and Written Opinion dated Sep. 4, 2014.
Australian Patent Application No. 2014202637; AU Examination Report dated Jan. 23, 2015.
Brazilian Patent Application No. BR1120140116377 Preliminary Office Action dated Jan. 7, 2020.
Canadian Patent Application No. 2,919,142; CA Examination Report dated May 31, 2016.
Chinese Patent Application No. 201480039991.2 First Office Action dated Dec. 29, 2016.
European Patent Application No. 14721736.8; Extended European Search Report dated Oct. 20, 2015.
European Patent Application No. 17150671.0; Extended European Search Report dated May 29, 2017.
U.S. Appl. No. 14/228,046; Final Office Action dated Nov. 27, 2020.
U.S. Appl. No. 14/228,054; Final Office Action dated Dec. 22, 2020.
U.S. Appl. No. 14/228,057; Office Action dated May 5, 2021.
U.S. Appl. No. 14/228,061; Final Office Action dated Apr. 29, 2021.
U.S. Appl. No. 14/228,061; Office Action dated Nov. 27, 2020.
U.S. Appl. No. 14/228,054; Final Office Action dated Jan. 3, 2022.
U.S. Appl. No. 14/228,061; Non-Final Office Action dated Dec. 8, 2021.
U.S. Appl. No. 14/228,057; Final Office Action dated Jan. 5, 2023.
U.S. Appl. No. 14/228,057; Office Action dated Sep. 2, 2022.
U.S. Appl. No. 29/782,644 Final Office Action dated May 11, 2022.
U.S. Appl. No. 29/782,643 Final Office Action dated May 11, 2022.
PCT Application No. PCT/US2020/032228 International Preliminary Report on Patentability dated Nov. 16, 2021.
European Patent Application No. 20804801.7; Extended European Search Report dated Apr. 20, 2023.
European Patent Application No. 20804801.7; Supplementary European Search Report dated May 10, 2023.
U.S. Appl. No. 29/782,645, Thien Nguyen, Mouthpiece, filed May 7, 2021.
U.S. Appl. No. 29/780,960, Thien Nguyen, Mouthpiece Mouth Prop, filed Apr. 27, 2021.
U.S. Appl. No. 29/782,638, Thien Nguyen, Mouthpiece, filed May 7, 2021.
U.S. Appl. No. 29/782,644, Thien Nguyen, Mouthpiece, filed May 7, 2021.
U.S. Appl. No. 29/782,643, Thien Nguyen, Mouthpiece, filed May 7, 2021.
U.S. Appl. No. 29/893,986 Ex Parte Quayle dated Aug. 15, 2023.
U.S. Appl. No. 18/217,304 Office Action dated Sep. 29, 2023.

* cited by examiner

DENTAL MOUTHPIECE

CROSS REFERENCE TO RELATED APPLICATIONS

The present application claims the priority benefit of U.S. Provisional Patent Application Ser. No. 62/846,353 filed May 10, 2019 entitled, "Dental Mouthpiece," the disclosures of which are incorporated herein by reference.

BACKGROUND OF THE INVENTION

1. Field of the Invention

The present invention generally relates to the field of dental mouthpieces. More specifically, the present invention relates to intraoral dental suction and isolation mouthpieces.

2. Description of Related Art

Various mouthpieces are currently used by dental health professionals, dental hygienists, and dental assistants in the field of dentistry. In the past, a dental patient has been treated by a traditional two-person team that comprises a dental professional and a dental assistant. Further, dental treatment may be provided by the team using many different types of dental equipment and materials. Such dental equipment and materials may include such items as an intraoral mirror, a bite block, a slow speed suction ejector, a high speed suction ejector, gauzes, cotton rolls, and dry angles. Each item of dental equipment may be used for different purposes, though some may be used in combination for some types of dental services. As such, a dental professional seeking to provide such dental services may need to use multiple items of such dental equipment. An important role of the dental assistant is therefore to assist the dental professional in coordinating the use of these multiple items of different equipment and materials.

There is, therefore, a need in the art for improved systems and methods of providing dental services in a more efficient, comfortable, and safe manner to the dental patient.

SUMMARY OF THE CLAIMED INVENTION

Embodiments of a dental mouthpiece formed in a curve are disclosed. Such a mouthpiece may comprise of a main body portion at a central part of the curve having a first end and a second end, a suction connector portion connected to the main body portion at the first end, and a cheek retractor portion connected to the main body portion at the second end.

In some embodiments, the main body portion, the suction connector portion, and the cheek retractor portion may be molded in one piece, preferably by injection molding. In an exemplary embodiment, the mouthpiece may be made of a material that is flexible, translucent, conductive to injection molding, high heat-resistant, and autoclavable. Such a material may include silicone. Because the mouthpiece may be made of a high heat-resistant and autoclavable material, such a mouthpiece may be reusable.

The main body portion may comprise of an anterior wall inside the curve and a posterior wall outside the curve. The anterior wall and the posterior wall may define an interior space, within which at least one connector connects the anterior wall to the posterior wall. At least one anterior intervening wall extends from the anterior wall partially towards the posterior wall, and at least one posterior intervening wall extends from the posterior wall partially towards the anterior wall. The anterior intervening walls and the posterior intervening walls each has alternating crests and troughs.

DETAILED DESCRIPTION

Embodiments of the present invention may include a mouthpiece that may be attached to a high-suction dental adapter for the purpose of assisting the dental staff during dental procedures through chair-side, hands-free suction, and isolation. Such a mouthpiece may comprise a main body portion, a cheek retractor portion, a suction connector portion, a stability bar, and a bite block. In some embodiments, any combination of the main body portion, cheek retractor portion, suction connector portion, a stability bar and bite block (and sub-portions thereof) may be molded in one piece, preferably by injection molding. In an exemplary embodiment, the mouthpiece may be made of a material that is flexible, resilient, at least translucent, and conducive to injection molding. Such a material may include thermoplastic elastomers known in the art.

Figure 1:
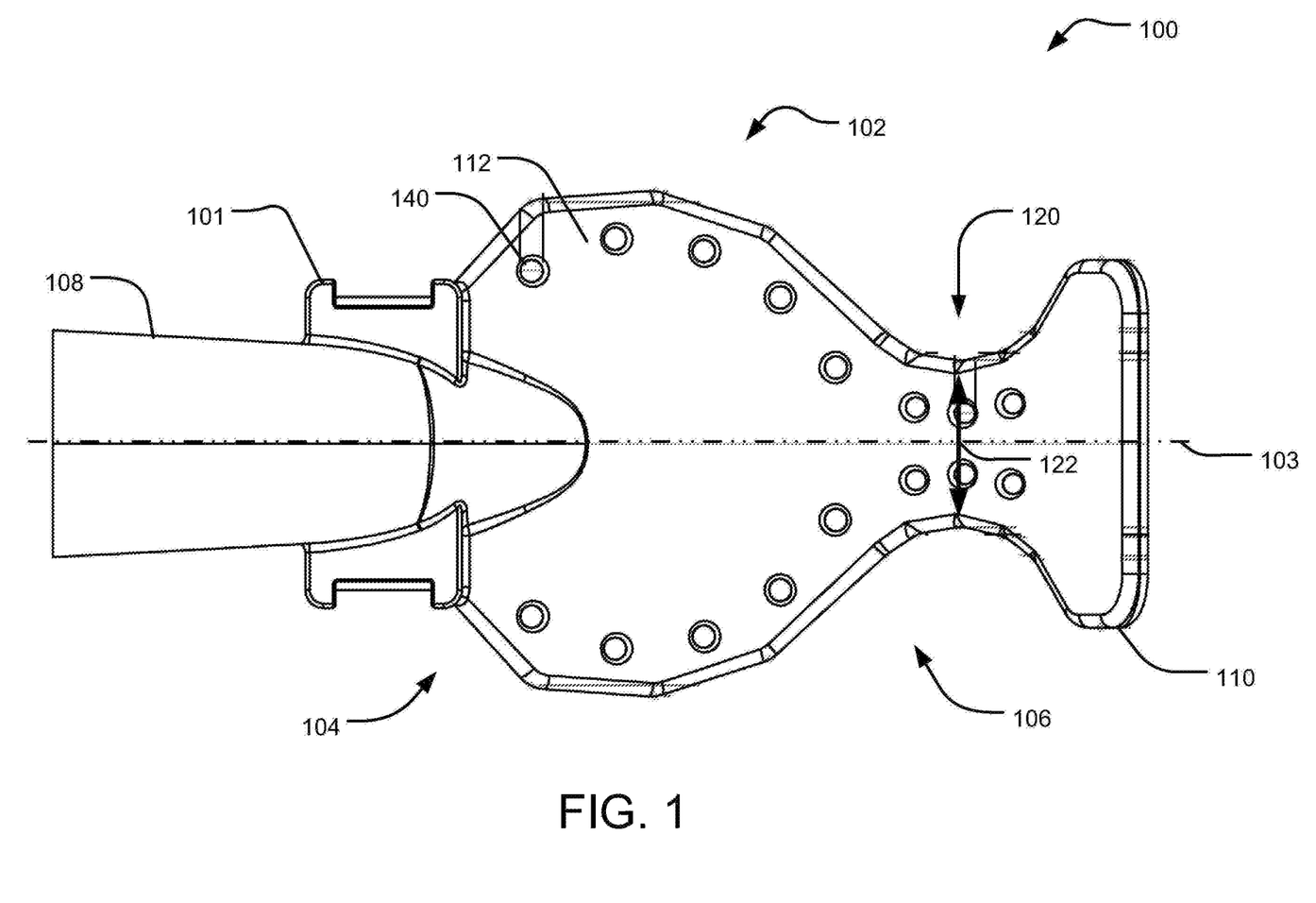
FIG. 1 is a top view of the dental mouthpiece.

FIG. 1 is a top view of the dental mouthpiece. A dental mouthpiece 100 includes a main body portion 102 having a first end 104 and a second end 106 opposite the first end 104. A longitudinal axis 103 may extend from the first end 104 to the second end 106. In the illustrated embodiment, a suction connector portion 108 may be coupled to the first end 104 and a cheek retractor portion 110 may be coupled to the second end 106, though in other examples the mouthpiece 100 may not have a suction connector portion 108 and/or a cheek retractor portion 110. A bite block 101 may also be integrated to the suction connector portion 108 near the first end 104 of the main body portion 102, though the bite block 101 may be positioned anywhere on the suction connector portion 108.

The main body portion 101 may include a neck 120 extending from the second end 106 to the cheek retractor portion 110. The neck 120 may have a width 122 that is less than a width of the main body portion 102, a width of the cheek retractor portion 110, and/or a width of the suction connector portion 108, though the width 122 may be greater than the width of the main body portion 102, the cheek retractor portion 110, and/or the suction connector portion 108 in other examples.

In the illustrated embodiment, the suction connector portion 108, the cheek retractor portion 110, the bite block 101, and the main body portion 102 are constructed as one piece, though in other examples each of the suction connector portion 108, the cheek retractor portion 110, the bite block 101, and/or the main body 102 may be separate pieces. For example, in some embodiments, the main body portion 102, the cheek retractor portion 110, and the suction connector portion 108 (and sub-portions thereof) may be molded as one-piece, preferably by injection molding and the bite block 101 may be a separate piece attachable to the suction connector portion 108. In an exemplary embodiment, the mouthpiece 100 may be made of a material that is flexible, resilient, translucent, and conducive to injection molding. Such a material may include thermoplastic elastomer.

Figure 2:
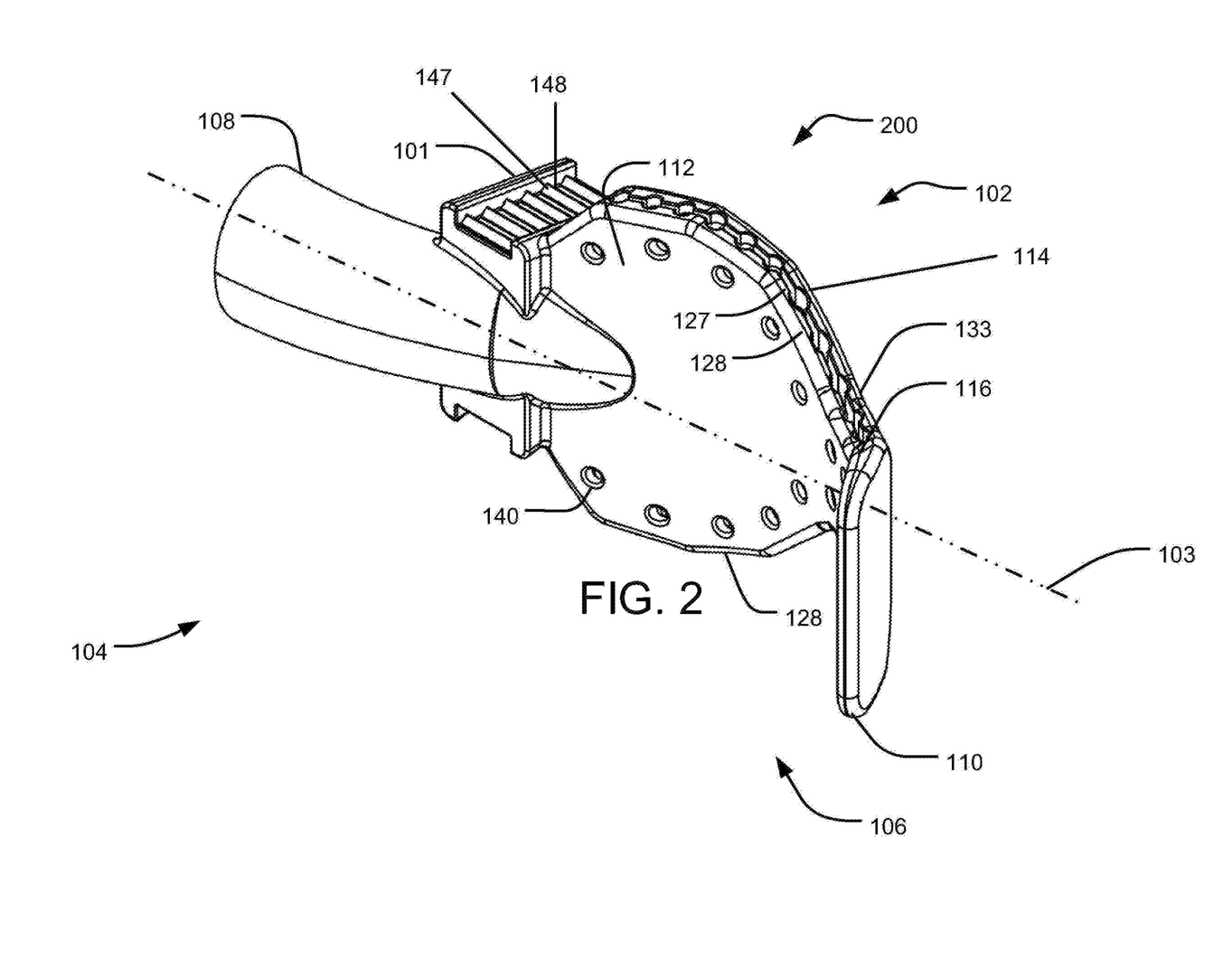
FIG. 2 is an isometric view of a dental mouthpiece shown in FIG. 1.

FIG. 2 is an isometric view of a dental mouthpiece shown in FIG. 1. As illustrated in FIG. 2, the main body portion 102 may be shaped in a curve. Because the mouthpiece 100 is made of a flexible and resilient material (e.g., thermoplastic elastomer), the mouthpiece 100 may be bent when placed in a patient's mouth to conform to the shape of the mouth. When properly positioned, the suction connector portion 108 may protrude from one side of the patient's mouth, while the main body portion 102 lies against the back of the patient's mouth, and the cheek retractor portion 110 presses against the patient's cheek on the opposite side of the patient's mouth.

The cheek retractor portion 110 may be configured to press against and retract a patient's cheek away from the patient's teeth on an opposite side of the patient's mouth than the side from which the connection portion 108 extends. The flexibility of the material used to form the mouthpiece 100 allows for some bending when placed in the patient's mouth, but the resilience of the material further allows the mouthpiece 100 to apply pressure against a part of the patient's mouth when the mouthpiece 100 is released from bending. The material is resilient enough, for example, to allow the cheek retractor portion 110 to press against the inside of the patient's cheek with such pressure being sufficient to move the cheek away from the patient's teeth. The cheek retractor portion 110 is illustrated as a hammerhead distal region, which may be attached to the main body portion 102. The cheek retractor portion 110 may be solid in some examples, though may be hollow in other examples.

The main body portion 102 may comprise an anterior wall 112 on an inner part of the curve and a posterior wall 114 (also seen in FIG. 4) on an outer part of the curve. The anterior wall 112 may face a front of the patient's mouth and the posterior wall 114 may face a back of the patient's mouth. The anterior wall 112 and the posterior wall 114 of the main body portion 102 may be configured in parallel to each other. The anterior wall 112 has a defined shape that may correspond to the defined shape of the posterior wall 114, though the anterior wall 112 may be a different shape than the posterior wall 114 in other examples. The defined shape may be wider at the first end 104 and narrower at the second end 106. In some embodiments, the shape corresponds to a shield shape though the shape may be, for example, a square, a straight line arrow, a rectangle, a star, an oval, a circle, or a shape that generally conforms to the intraoral shape of the patient's mouth. Differently-sized mouthpieces may be provided for differently-sized mouths of adults and children. Part of the shape at the first end 104 may be formed with thicker walls than the rest of the main body portion 102. Such thickening may provide additional stability at the first end 104. When positioned within the mouth of a patient, the anterior wall 112 and the posterior wall 114 are capable of blocking an airway of the patient, while the bite block 101 is positioned between the patient's teeth, the suction connector portion 108 extends from one side of the patient's mouth, and the cheek retractor portion 110 presses against the cheek on the opposite side of the patient's mouth.

The main body portion 102 may also include openings 140 located on the anterior wall 112 and/or the posterior wall 114. Such openings 140 (e.g., perforations, slit, aperture, etc.) allow for suction of air, fluids, and small debris from the patient's mouth through the openings 140 and into the interior space 126, and into the suction connector portion 108 towards a suction source. The openings 140 may be positioned on a perimeter of the shape of the anterior wall 112 and/or the posterior wall 114. In the same example, the openings 140 may be positioned on either side of the neck 120 on the anterior wall 112 and/or the posterior wall 114. In another example, the openings 140 are apertures. In the same example, the apertures are each the same size, though in other examples some or all of the apertures may be different sizes.

Figure 3:
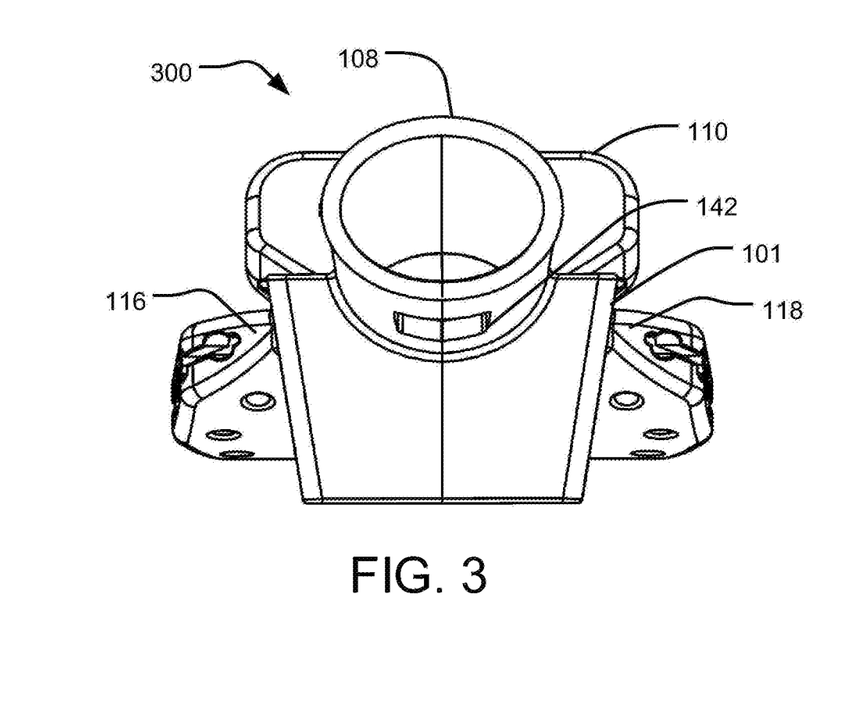
FIG. 3 is a rear view of the dental mouthpiece shown in FIG. 1.

FIG. 3 is a rear view of the dental mouthpiece shown in FIG. 1. As visible in FIG. 3, the suction connector portion 108 may be oval-shaped and also attached to the main body portion 102. The suction connector portion 108 may be formed with thicker walls than the main body portion 102 and configured to attach to a high-suction vacuum adapter and to assist in transferring water, saliva, and debris from the interior space 126 to the external adapter for removal. The suction connector portion 108 may also include an internal stop to assist in sliding the mouthpiece onto the adapter to a desired depth.

The superior wall 116 in FIG. 3 may be used herein to refer to the side that rests against a roof of a patient's mouth when placed therein, and the inferior wall 118 may be used to refer to the side that rests against the floor of the patient's mouth. The superior wall 116 and inferior wall 118 may be formed identically, which may allow for the mouthpiece to change orientation such that the superior wall 116 may appear as the inferior wall 118 and vice versa, in the new orientation. When in use, the superior wall 116 and the inferior wall 118 of the main body portion 101 may serve to protect and separate the top of the mouth and the bottom of the mouth/tongue. In addition, the main body portion 101 may also serve to protect the back of the mouth (e.g., throat and airway) from falling debris.

Figure 4:
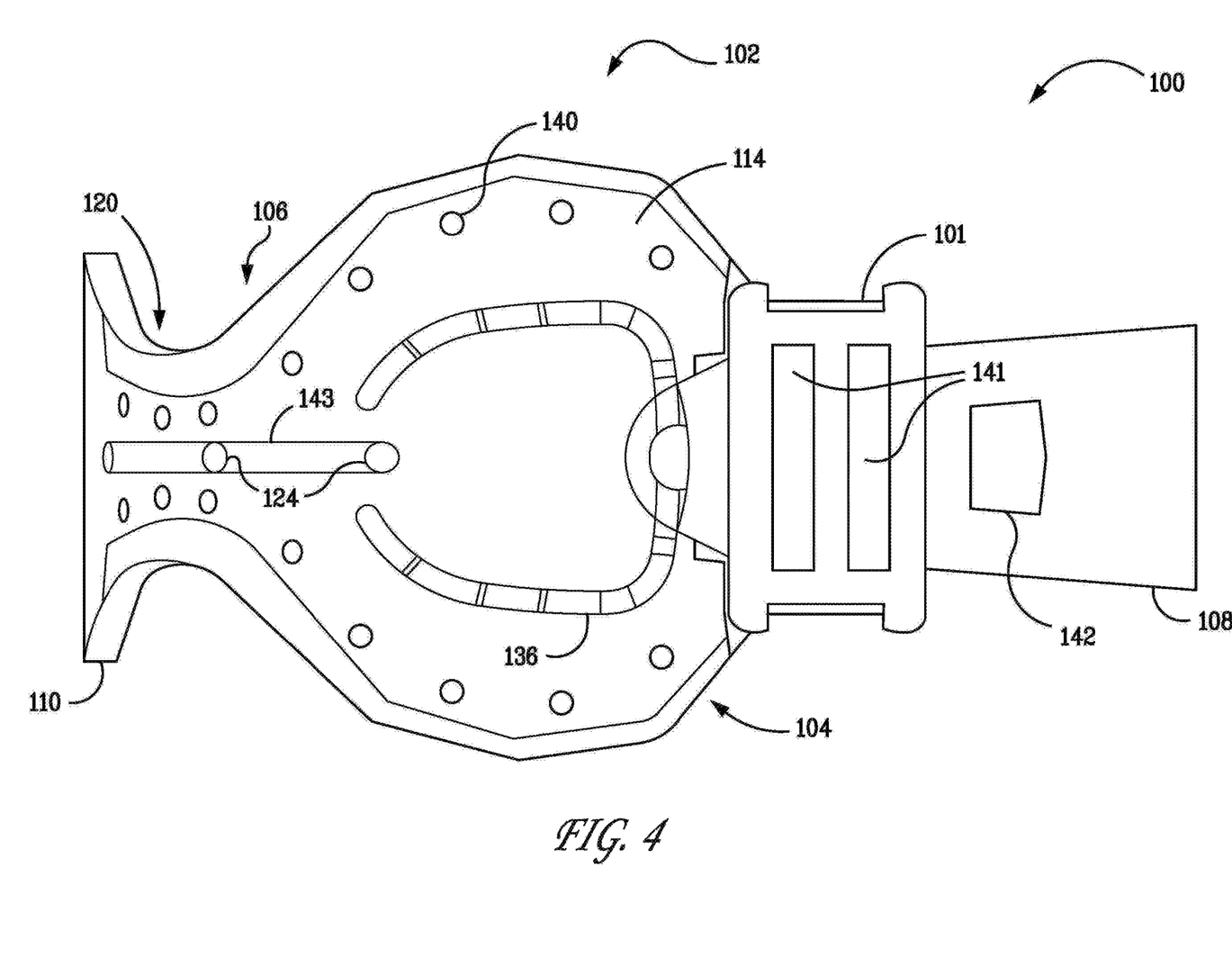
FIG. 4 is a bottom view of the dental mouthpiece shown in FIG. 1.

FIG. 4 is a bottom view of the dental mouthpiece shown in FIG. 1. The anterior wall 112 and the posterior wall 114 may be connected to each other at by at least one connector 124. In some embodiments, the suction connector portion 108 may have a cutout 142 (e.g., which may be shaped as a logo, a rectangular notch, a square notch, or a circular notch, or any shaped notch) providing extra interlocking with a corresponding protrusion (e.g., which may also be shaped as a logo, a rectangular protrusion, a square protrusion, or a circular protrusion, or any shaped protrusion) on an external high-suction vacuum adapter.

The bite block 101 may be reinforced by bite block openings 141 to create cavities in the bite block to result in a more stable bite block. In an embodiment, the bite block openings 141 may be two parallel rectangular openings that open at the bottom of the bite block. The bite block openings 141 may extend up to the suction connector portion 108 but not extending past the thickness of the suction connector portion 108.

Figure 5:
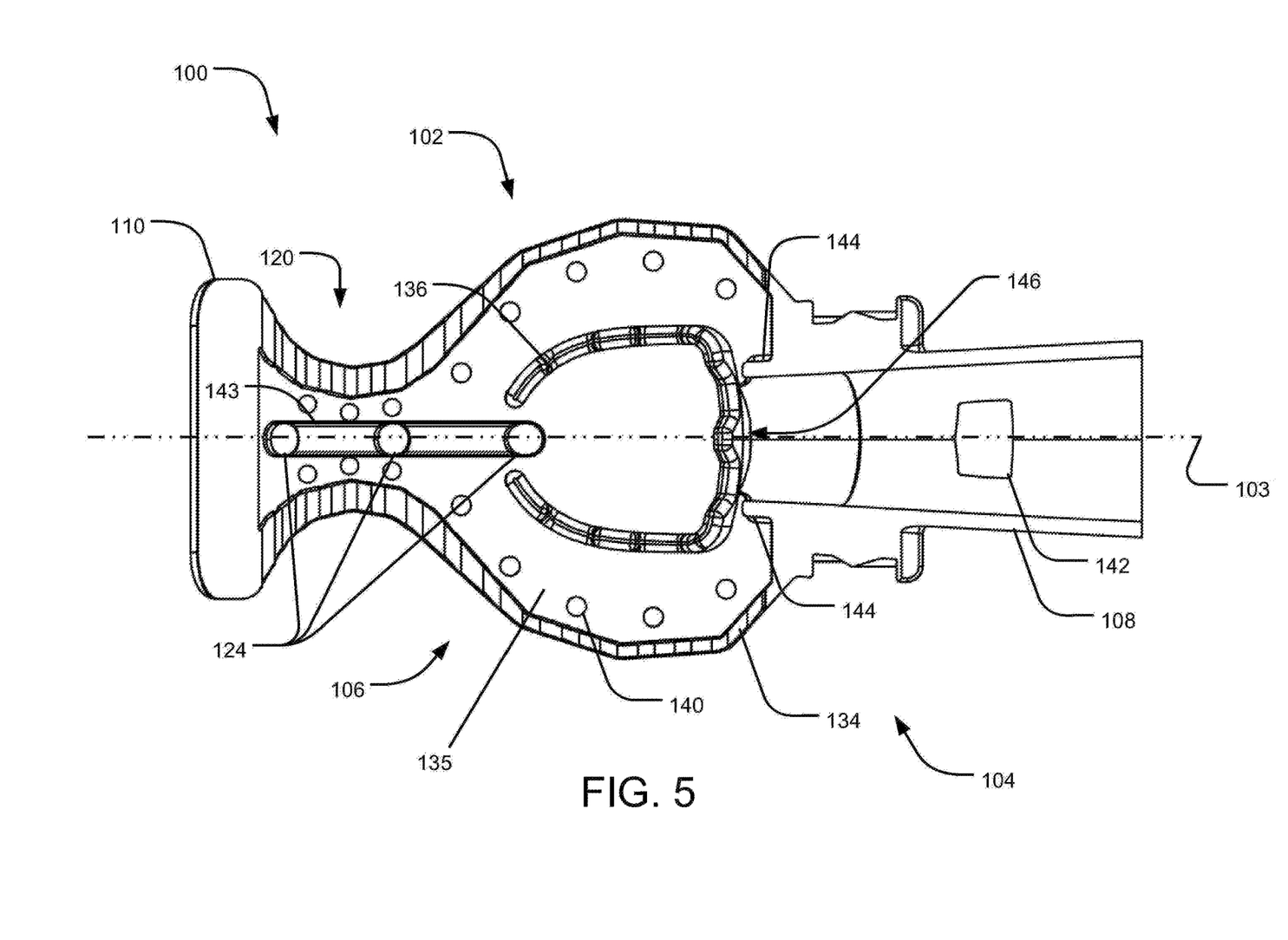
FIG. 5 is a coronal top cross section view of the dental mouthpiece shown in FIG. 1.

FIG. 5 is a coronal top cross section view of the dental mouthpiece shown in FIG. 1. The main body portion 102 may include the bridge structure 136 that protrudes from the interior surface 135 of the posterior wall 114, as shown in FIG. 5 and also visible in FIGS. 7 and 8. In some embodiments, the bridge structure 136 may follow the shape of a logo (e.g., an arrowhead or shield). The bridge structure may have a gap at the tip of the arrowhead shape, creating an open arc instead of a point of an arrow. In some embodiments, the bridge structure 136 may be centrally-located in the main body portion 110 of the mouthpiece 100. In some examples, such bridge structure 136 may protrude from the interior surface 135 in a wave shape with bridge crests 137 and bridge troughs 138. In other embodiments, the bridge structure 136 may protrude in the shape of battlements or trapezoids. The bridge crests 137 provide a plurality of contact points that are generally separate from the anterior wall 112. The bridge crests 137 near the opening 146 of the suction connector portion 108 may have a greater height than the bridge crests 137 further from the opening 146, as visible in FIGS. 7 and 8. The bridge crests 137 near the opening 146 of the suction connection portion 108 may also be longer than the bridge crests 137 further away from the suction connection portion 108 as shown later in FIG. 8. The bridge troughs 138 may be substantially flush or extend above the interior surface 135. The bridge crests 137 contact the anterior wall 112 during suction to keep the anterior wall 112 spaced away from the posterior wall 114 during suction, thereby preventing collapse of the anterior wall 112 or the posterior wall 114 into the interior space 126 so that debris and/or water can be evacuated through the interior space 126. Meanwhile, the bridge troughs 138 provide gaps that allow for suction of air, fluids, and small debris through the bridge structure 136. In other examples, the bridge structure 136 may be smooth, may include sharp crests and sharp troughs, circular crests and circular troughs, square crests and square troughs, or shape or combination of shapes of crests and troughs.

Figure 7:
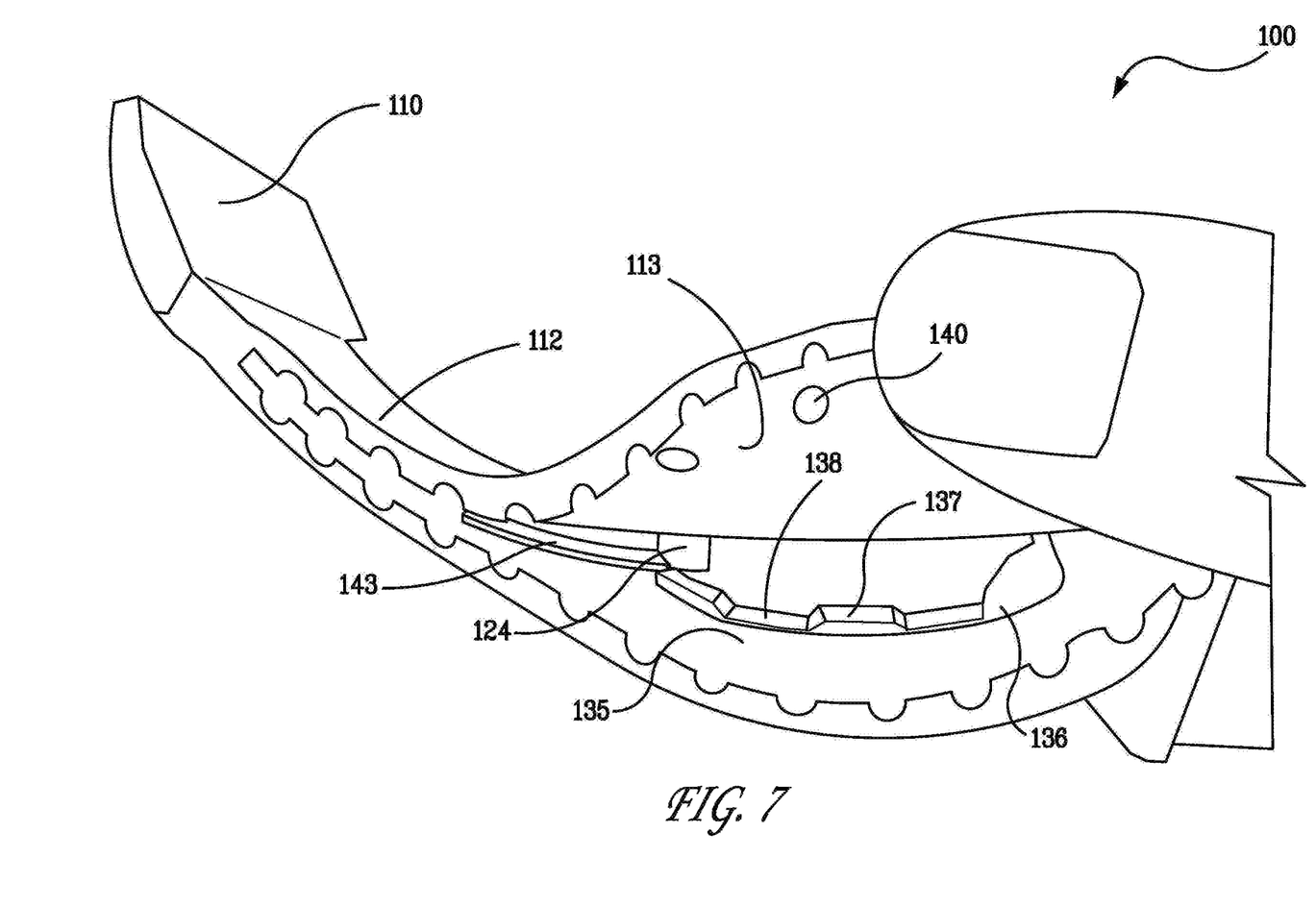
FIG. 7 is a side of the dental mouthpiece shown in FIG. 1 with an anterior wall of the mouthpiece pulled away from a posterior wall of the mouthpiece.

The main body portion 102 may further include a stability bar 143, shown in FIG. 5 and also visible in FIG. 7, that extends from approximately the center of the main body portion 102 toward the cheek retractor portion 110. Such stability bar 143 may protrude from the interior surface 135 of the posterior wall 114 along the longitudinal axis 103. In an embodiment, the stability bar 143 begins from the open arc of the bridge structure 136 and continue along the longitudinal axis 103 towards the second end 106 past the neck 120 and ends before reaching the cheek retractor portion 110. The stability bar 143 may protrude from the interior surface 135 of the posterior wall 114 towards the interior surface 113 of the anterior wall 112. The stability bar 143 may be of any height ranging from the height of the interior space 126 or any height less than the interior space 126. In an embodiment, the stability bar 143 may have attached connectors 124 at specific locations that may attach the anterior wall 112 to the posterior wall 114. The connectors 124 on the stability bar 143 may assist with retraction, stability, support and curvature of the mouthpiece 100 during suction. In an exemplary embodiment, there may be multiple connectors 124 aligned with the stability bar 143 the stability bar 143, though the stability bar 143 may not be aligned with the at least one connector 124 in other examples.

Figure 6:
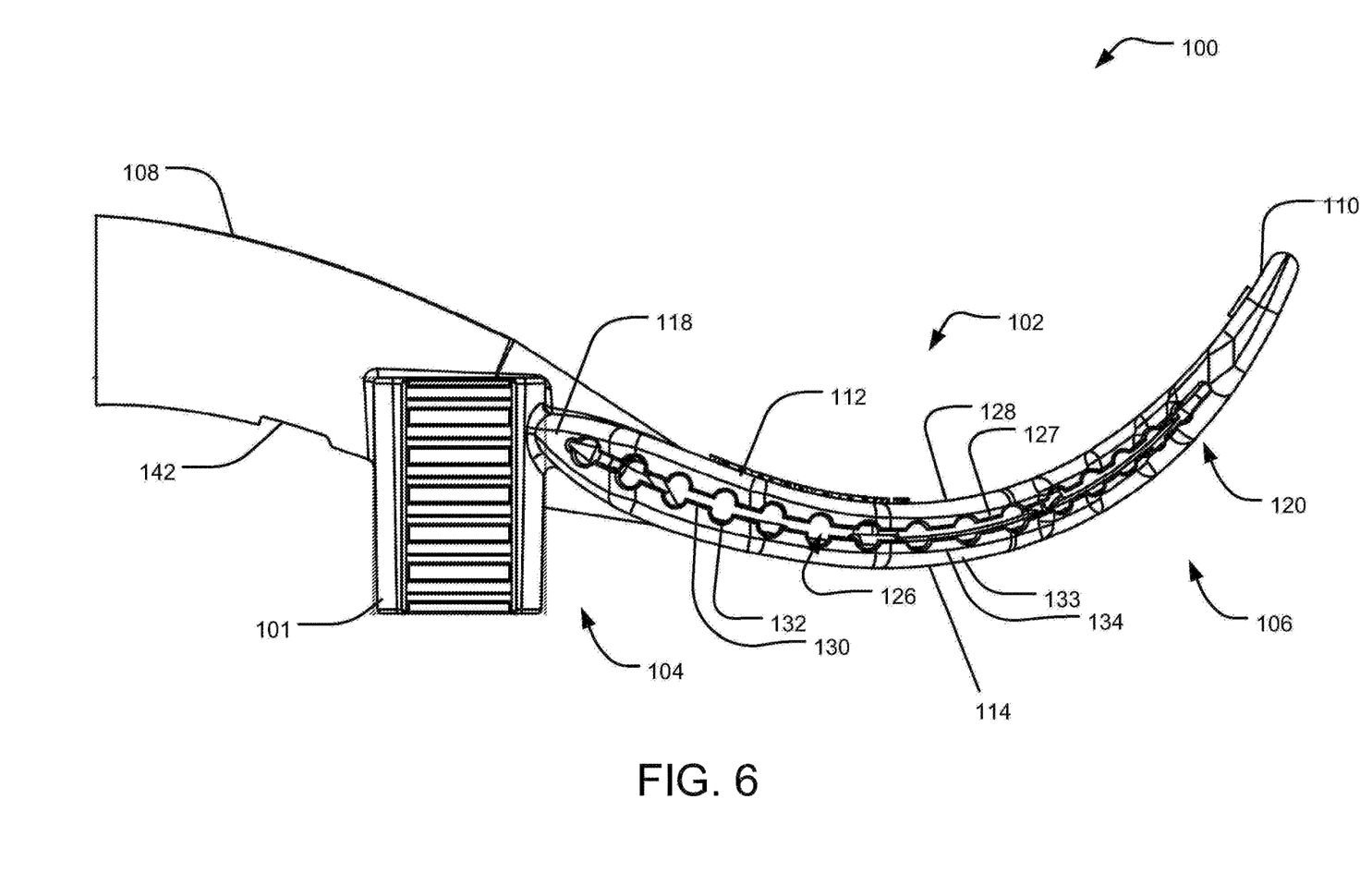
FIG. 6 is a side view of the dental mouthpiece shown in FIG. 1.

FIG. 6 is a side view of the dental mouthpiece shown in FIG. 1. FIG. 6 illustrates the view of the inferior side that rests against the floor of the patient's mouth. The anterior wall 112 and the posterior wall 114 are spaced from each other and define the interior space 126. Other than the at least one connector 124, a stability bar 143, and a bridge structure 136, the interior space 126 is generally open and unobstructed, thereby allowing for suction to flow throughout the interior space 126. The interior space 126 between the anterior wall 112 and the posterior wall 114 generally follows the same defined shape of the anterior wall 112 and the posterior wall 114. In one example, the interior space 126 extends through the neck 120, though in other examples the interior space 126 may not extend through the neck 120. In yet other examples, the interior space 126 extends through the neck 120 and into the cheek retractor portion 120.

At least one anterior intervening wall 127 may extend from at least one edge 128 of the anterior wall 112 partially towards the posterior wall 114 and may have a thickness that extends from the at least one edge 128 to a mid-point between the anterior wall 112 and the posterior wall 114. The span of such anterior intervening wall 127 therefore may not extend the entire distance between the anterior wall 112 and the posterior wall 114. The thickness of such anterior intervening wall 127 may increase from the cheek retractor portion 110, through the neck 120, and to the first end 104. Such increasing depth may provide for increased rigidity at the first end 104. Such anterior intervening wall 127 may further be ridged in some embodiments, or have a smooth edge in other embodiments. In one example, the anterior intervening wall 127 includes an alternating crest 130 and trough 132. In the illustrated embodiment, the crests 130 are a flat surface and the troughs 132 are a cylindrical cutout surface, though the crests 130 and the troughs 132 may be any shape. In some examples, the crests 130 and the troughs 132 extend the entire depth of the anterior intervening wall 127, though in other examples the crests 130 and/or the troughs 132 may extend partially along the anterior intervening wall 127. The crests 130 and the troughs 132 may provide further retraction, stability, support and curvature to the mouthpiece 100.

The posterior wall 114 may have a corresponding at least one posterior intervening wall 134 that extends from at least one edge 133 of the posterior wall 114 and partially extends towards the anterior wall 112. The posterior intervening wall 134 may likewise exhibit ridges that are the same, a mirror image, or different from the anterior intervening wall 127. In one example, the ridges of the anterior intervening wall 127 may be aligned with the ridges of the posterior intervening wall 134, as shown in FIG. 6. In combination, the anterior intervening wall 127 and the posterior intervening wall 134 and their respective aligned ridges may form an open mesh between the anterior wall 112 and the posterior wall 114. Such open mesh may follow the edges 128, 133 of each of the anterior wall 112 and the posterior wall 114 from the first end 104 to the second end 106. The open mesh between the anterior intervening wall 127 and the posterior intervening wall 134 allows for suction of air, fluids, and small debris from patient's mouth, through the mesh into the interior space 126 and into the suction connector portion 108 towards a suction source.

The anterior intervening wall 127 may join with the posterior intervening wall 134 at the superior wall 116 and the inferior wall 118 at near the suction connector portion 108 of the main body at the first end 104. The anterior intervening wall 127 may also join with the posterior intervening wall 134 at the superior wall 116 and the inferior wall 118 near the cheek retractor portion 110 at the second end 106. In some embodiments, the anterior intervening wall 127 may join with the posterior intervening wall 134 at the cheek retractor portion 110.

FIG. 7 is a side of the dental mouthpiece shown in FIG. 1 with an anterior wall of the mouthpiece pulled away from a posterior wall of the mouthpiece. The at least one connector 124 may span the distance between the anterior wall 112 and the posterior wall 114 within the interior space 126. In other words, the connector 124 may be attached to an interior surface 135 of the posterior wall 114 and to an interior surface 113 of the anterior wall 112. The at least one connector 124 may provide structural rigidity to the mouthpiece 100 and may be a pillar, column, wall, or the like. In the illustrated example, the at least one connector 124 includes three connectors, each in the shape of a pillar and linearly spaced from each other.

Figure 8:
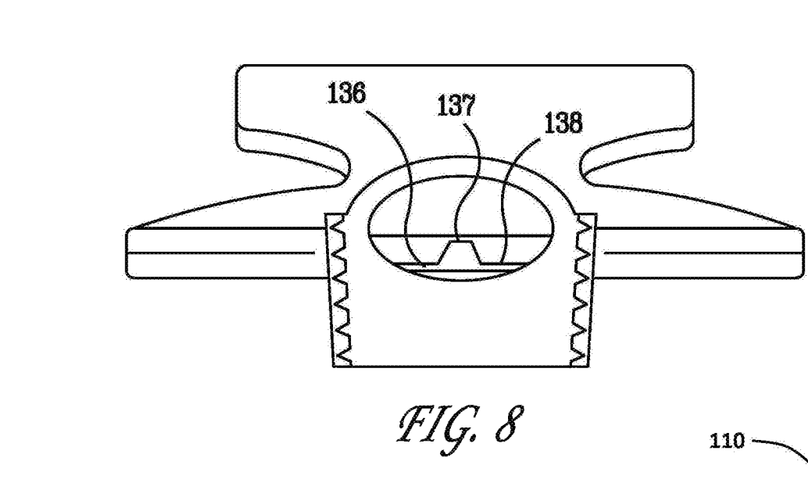
FIG. 8 is a transverse cross section view of the dental mouthpiece shown in FIG. 1 at the intersection between the suction connector and the main body.

FIG. 8 is a transverse cross section view of the dental mouthpiece shown in FIG. 1. The bridge crests 137 near the opening 146 of the suction connector portion 108 may have a greater height than the bridge crests 137 further from the opening 146. The bridge crests 137 near the opening 146 of the suction connection portion 108 may also be longer than the bridge crests 137 further away from the suction connection portion 108.

Figure 9:
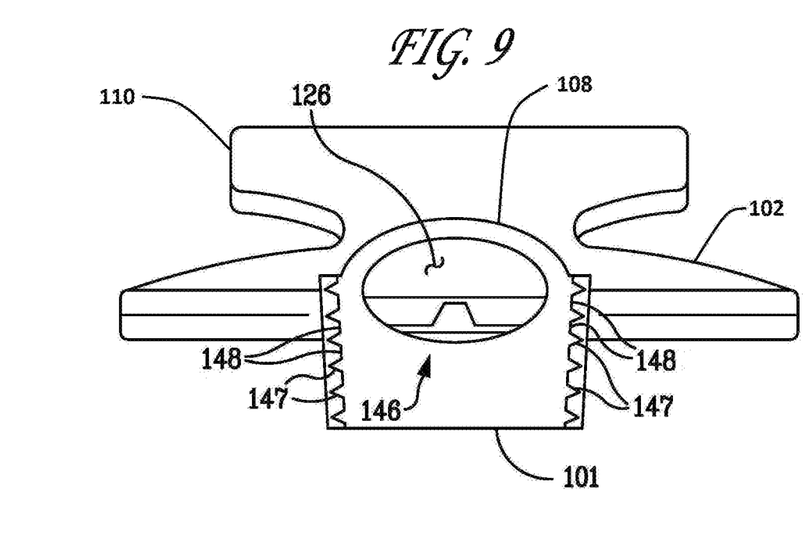
FIG. 9 is a transverse cross section view of the dental mouthpiece shown in FIG. 1 at the intersection between the suction connector and the main body.

FIG. 9 is a transverse cross section view of the dental mouthpiece in FIG. 1. FIG. 9 illustrates where the suction connector attaches to the main body. As visible in FIG. 9, the suction connector portion 108 may be oval-shaped and also attached to the main body portion 102 in a seamless transition until the main body reaches the bridge structure 136, where the bridge crests 137 and the bridge troughs 138 may partially block the opening of the main body portion 102 near the suction connector portion 108. The bite block 101 is attached on the outside of the suction connector portion 108 such a manner that the bite block does not interrupt the opening of the suction connector portion 108.

The suction connector portion 108 may include an opening 146 (also shown in FIG. 5), that opens into an interior space 126 of the main body portion 102 to allow for fluid communication between the interior space 126 and the suction connector portion 108. At least one suction connector portion wall 144 may extend from the anterior wall 112 to the posterior wall 114 near the opening 146 of the suction connector portion 108 to prevent collapse of the anterior wall 112 and the posterior wall 114 during suctioning. The at least one suction connector portion wall 144 includes a pair of walls positioned on either side of the opening 146 of the suction connector portion 108.

The bite block 101 may include bite block crests 147 and bite block troughs 148 on either sides of the bite block to create greater traction and support for the bite block. In an embodiment, the bite block crests 147 and bite block troughs 148 may create jagged shape or wave shape on either sides of the bite block, although the bite block crests 147 and bite block troughs 148 may be in any shape.

Figure 10:
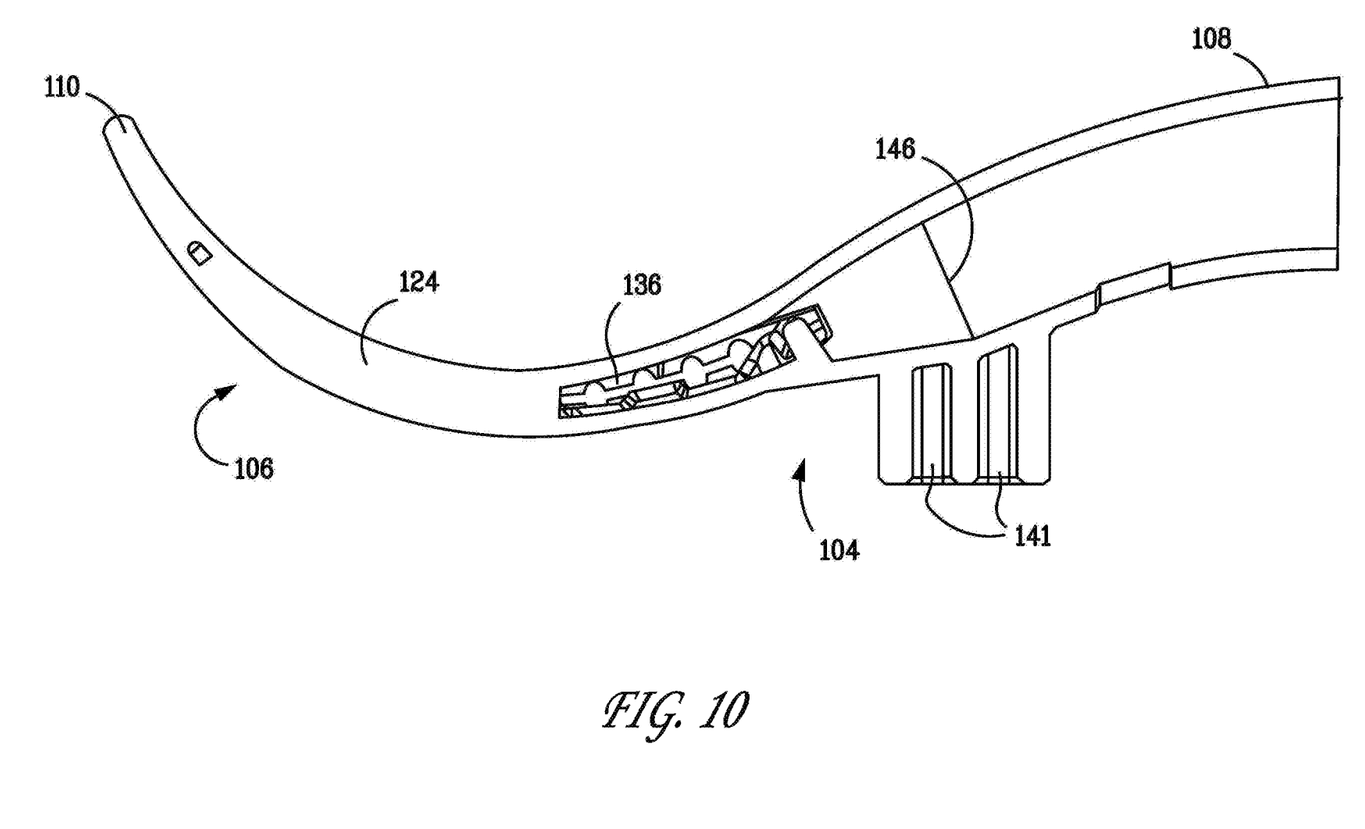
FIG. 10 is a longitudinal cross section view of an embodiment of the dental mouthpiece shown in FIG. 1 with a wall connector.

FIG. 10 is a cross section view of an embodiment of the dental mouthpiece shown in FIG. 1 with a wall connector. In this embodiment, the connector 124 connects the anterior wall 112 with the posterior wall 114 at the longitudinal axis 103 as a solid wall. The connector 124 extends from the neck 120 at the second end 106 some distance away from the cheek retractor portion 110 towards the first end 104 along the longitudinal axis 103 and stops near the opening of the bridge structure 136 around the mid-point of the main body portion 102. In other embodiment, the connector 124 may extend along the longitudinal axis 103 and stop anywhere within the interior space 126 of the main body portion.

Figure 11:
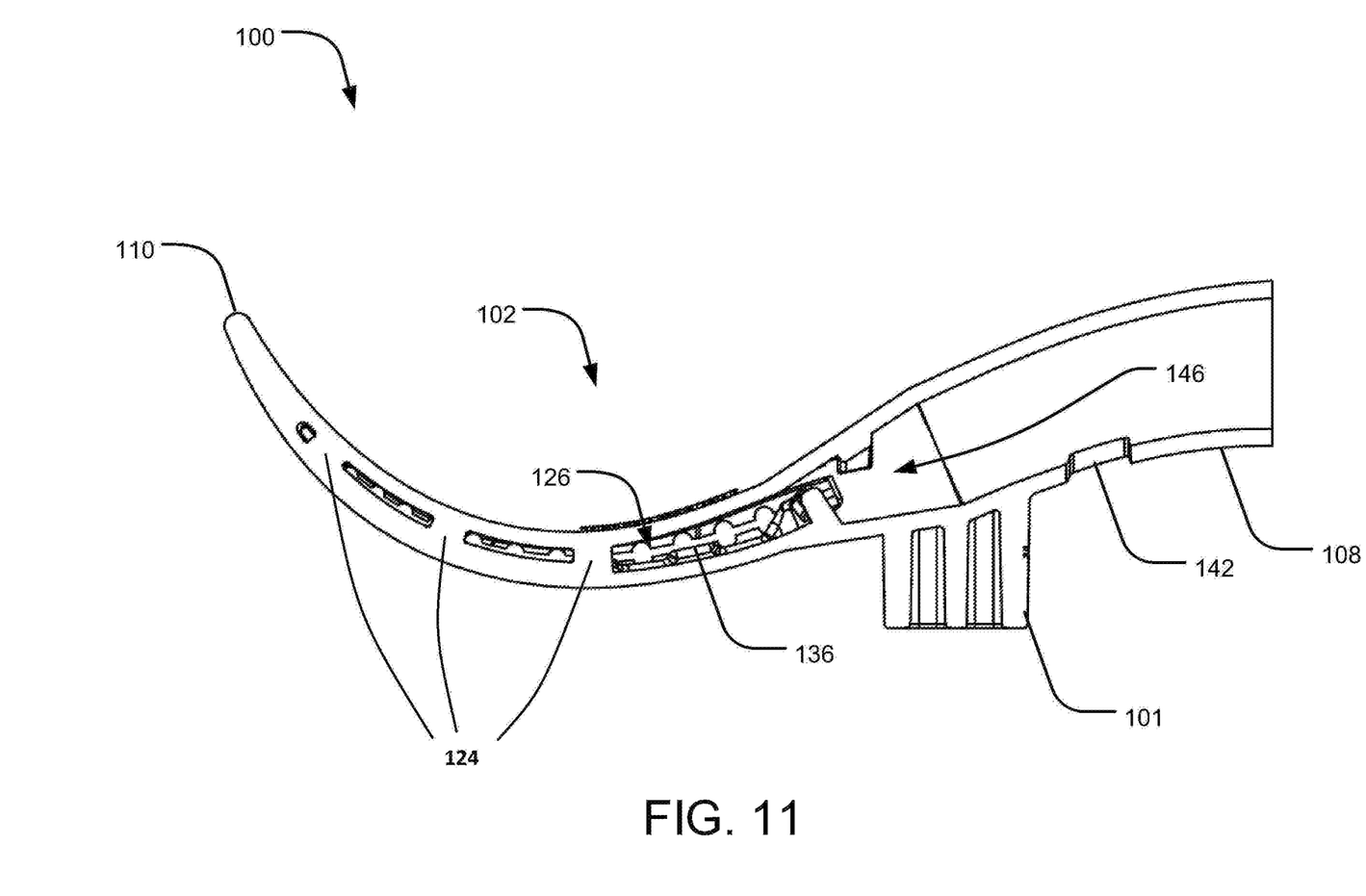
FIG. 11 is a longitudinal cross section view of an embodiment of the dental mouthpiece shown in FIG. 1 with column connectors.

FIG. 11 is a longitudinal cross section view of an embodiment of the dental mouthpiece shown in FIG. 1 with column connectors. In this embodiment, the connector 124 connects the anterior wall 112 with the posterior wall 114 at the longitudinal axis 103 as three evenly spaced cylindrical pillars in line with the stability bar 143. A first connector is positioned in the main body portion 102, a second connector is positioned near the neck 120, and a third connector is spaced near the cheek retractor portion 110. The linear spacing of the three connectors may provide additional rigidity to the neck 120, while maintaining a narrow width 122 of the neck 120. In other examples, such connectors 124 may be located in the area where a positioned mouthpiece 100 begins to wrap from one side of the mouth, to the back of the mouth, then to the other side of the mouth, thereby assisting in shaping the mouthpiece 100 to the general intraoral shape of a patient's mouth. In other examples, the at least one connector 124 may include one connector, two connectors, or more than two connectors and each connector may be positioned anywhere on the mouthpiece 100. In one example, the at least one connector 124 is a rib that extends from the main body portion 102, through the neck 120, and to the cheek retractor portion 110.

The mouthpiece as described herein may be used with a one-piece, autoclavable, high-suction vacuum adapter. Such a high-suction vacuum body adapter may be made of a single homogenous material. Having a single lever design, such a vacuum adapter may function in the same manner as all the current high-suction vacuum evacuators and saliva ejectors in controlling the removal of water, saliva, and debris from the oral cavity to the outside vacuum source. The single lever may be designed to control the removal of water, saliva, and debris from the at least partially enclosed so main body through a single, large evacuation conduit within the suction connector portion.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

What is claimed:

1. A dental mouthpiece formed in a curve, the dental mouthpiece comprising:
a main body portion at a central part of the curve having a first end and a second end, the main body portion having an anterior wall inside the curve and a posterior wall outside the curve, the anterior wall and the posterior wall defining an interior space corresponding to a distance between the anterior wall and the posterior wall, at least one connector connecting the anterior wall to the posterior wall, an anterior intervening wall protruding from and extending along an edge of the anterior wall, the anterior intervening wall having a span that extends partially across the distance of the interior space towards the posterior wall, and a posterior intervening wall extending along an edge of the posterior wall partially across the distance towards the anterior wall, and wherein an edge of the span of the anterior intervening wall has alternating crests and troughs that extend different distances partially across the interior space towards the posterior intervening wall;
a suction connector portion connected to the first end, the suction connector portion connecting the interior space to a vacuum suction source; and
a cheek retractor portion connected to the second end.

2. The mouthpiece of claim 1, wherein the at least one connector includes at least one of a wall spanning longitudinally in the main body portion in the interior space or a pillar.

3. The mouthpiece of claim 1, further comprising a bridge structure that includes one or more protrusions protruding from the posterior wall within the interior space, wherein the protrusions include spaced crests and troughs.

4. The mouthpiece of claim 3, wherein the protrusions vary in height and length.

5. The mouthpiece of claim 1, wherein at least one of the anterior intervening wall and the posterior intervening wall includes a plurality of portions of varying heights relative to a longitudinal axis of the mouthpiece.

6. The mouthpiece of claim 1, wherein the anterior intervening wall and the posterior intervening wall meet at a point where the suction connector meets the main body portion.

7. The mouthpiece of claim 1, wherein the anterior intervening wall and the posterior intervening wall meet at a point where the main body portion meets the cheek retractor portion.

8. The mouthpiece of claim 1, further comprising a bite block integrated to the suction connector portion, wherein the bite block provides crush-resistance during biting by a patient.

9. The mouthpiece of claim 1, wherein the main body portion, the suction connector portion, and the cheek retractor portion are formed by injection-molding as one piece.

10. The mouthpiece of claim 1, wherein a material that forms the main body portion, the suction connector portion, and the cheek retractor portion is a flexible, translucent, high heat-resistant, autoclavable silicone-based material.

11. The mouthpiece of claim 1, wherein the posterior wall further includes a stability bar protruding from an interior surface of the posterior wall and along a longitudinal axis of the main body portion.

12. The mouthpiece of claim 11, wherein the at least one connector includes a plurality of evenly spaced connectors located along the stability bar.

13. The mouthpiece of claim 1, wherein the suction connector portion comprises a cutout corresponding to a protrusion on a vacuum adapter to provide an interlocking fit.

14. The mouthpiece of claim 1, where in the suction connector portion connects to the vacuum suction source, wherein activation of the vacuum suction source provides suction of fluids from the interior space of the main body portion.

15. The mouthpiece of claim 14, wherein the activation of the vacuum suction source draws fluids from an exterior of the main body portion into the interior space of the main body portion.

16. The mouthpiece of claim 1, wherein the span of the anterior intervening wall extends from the edge of the anterior wall to at least a mid-point of the interior space between the anterior wall and the posterior wall.

17. A dental mouthpiece comprising:
a main body portion having a first end and a second end, the main body portion comprising:
an anterior wall,
a posterior wall spaced at a distance from the anterior wall, wherein an interior space corresponding to the distance between the anterior wall and the posterior wall is defined by the anterior wall and the posterior wall,
at least one connector that connects the anterior wall to the posterior wall within the interior space,
at least one intervening wall protruding from and extending along an edge of the anterior wall or the posterior wall, the at least one intervening wall having a span that extends partially across the distance of the interior space, and wherein an edge of the span of the at least one intervening wall has a plurality of alternating crests and troughs that extend different distances partially across the interior space, and
a neck extending from the second end of the main body portion, wherein a width of the neck is less than a width of the main body portion at the first end;
a suction connector portion connected to the first end of the main body portion, the suction connector portion further configured to connect the interior space to a vacuum suction source; and
a cheek retractor portion connected to the neck that extends from the second end of the main body portion, wherein the width of the neck is less than a width of the cheek retractor portion.

18. The mouthpiece of claim 17, wherein the at least one intervening wall includes a plurality of portions of varying heights relative to a longitudinal axis of the mouthpiece.

19. The mouthpiece of claim 17, further comprising a bite block integrated to the suction connector portion, wherein the bite block provides crush-resistance during biting by a patient.

20. The mouthpiece of claim 17, wherein the main body portion, the suction connector portion, and the cheek retractor portion are formed by injection-molding as one piece.

21. The mouthpiece of claim 17, wherein the suction connector portion comprises a cutout corresponding to a protrusion on a vacuum adapter to provide an interlocking fit.

22. The mouthpiece of claim 17, where in the suction connector portion connects to the vacuum suction source, wherein activation of the vacuum suction source provides suction of fluids from the interior space of the main body portion.

23. The mouthpiece of claim 22, wherein the activation of the vacuum suction source further draws fluids from an exterior of the main body portion into the interior space of the main body portion.

* * * * *